(12) United States Patent
Abjanic et al.

(10) Patent No.: US 7,590,729 B2
(45) Date of Patent: *Sep. 15, 2009

(54) METHOD AND APPARATUS FOR CONTENT BASED SWITCHING

(75) Inventors: John B. Abjanic, San Diego, CA (US); Tak F. Sze, San Diego, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/464,020

(22) Filed: Aug. 11, 2006

(65) Prior Publication Data

US 2006/0288122 A1    Dec. 21, 2006

Related U.S. Application Data

(63) Continuation of application No. 09/927,255, filed on Aug. 10, 2001, now Pat. No. 7,096,270, which is a continuation-in-part of application No. 09/549,041, filed on Apr. 13, 2000, now Pat. No. 6,732,175.

(51) Int. Cl.
    *G06F 15/173* (2006.01)
(52) U.S. Cl. .................... 709/224; 709/244
(58) Field of Classification Search .............. None
    See application file for complete search history.

(56) References Cited

U.S. PATENT DOCUMENTS

| | | | |
|---|---|---|---|
| 5,634,010 A | 5/1997 | Ciscon et al. | |
| 5,678,010 A | 10/1997 | Pittenger et al. | |
| 5,987,500 A | 11/1999 | Arunachalam | |
| 6,006,264 A | 12/1999 | Colby et al. | |
| 6,012,098 A | 1/2000 | Bayeh et al. | |
| 6,032,190 A | 2/2000 | Bremer et al. | |
| 6,091,724 A | 7/2000 | Chandra et al. | |
| 6,226,675 B1 | 5/2001 | Meltzer et al. | |
| 6,408,311 B1 | 6/2002 | Baisley et al. | |
| 6,480,860 B1 | 11/2002 | Monday | |
| 6,480,865 B1 | 11/2002 | Lee et al. | |
| 6,578,068 B1 * | 6/2003 | Bowman-Amuah | 709/203 |
| 6,629,127 B1 | 9/2003 | Deen et al. | |
| 6,732,175 B1 | 5/2004 | Abjanic | |
| 6,742,015 B1 * | 5/2004 | Bowman-Amuah | 718/101 |
| 7,020,681 B1 | 3/2006 | Ayyagari et al. | |
| 7,082,476 B1 * | 7/2006 | Cohen et al. | 709/246 |
| 7,096,270 B2 * | 8/2006 | Abjanic et al. | 709/229 |
| 7,177,909 B2 * | 2/2007 | Stark et al. | 709/206 |
| 7,366,781 B2 | 4/2008 | Abjanic | |

* cited by examiner

*Primary Examiner*—John B. Walsh
(74) *Attorney, Agent, or Firm*—Kacvinsky LLC

(57) ABSTRACT

Various embodiments are described for performing pattern matching for content based switching. In one embodiment, an apparatus may include a document parser and a pattern parser. The document parser may be arranged to parse a document having transaction information and to create a document object from the transaction information. The pattern parser may be arranged to parse pattern information of a pattern for one or more elements according to a predefined pattern object data structure and to place the elements in appropriate blocks within the pattern object data structure. Other embodiments are described and claimed.

17 Claims, 16 Drawing Sheets

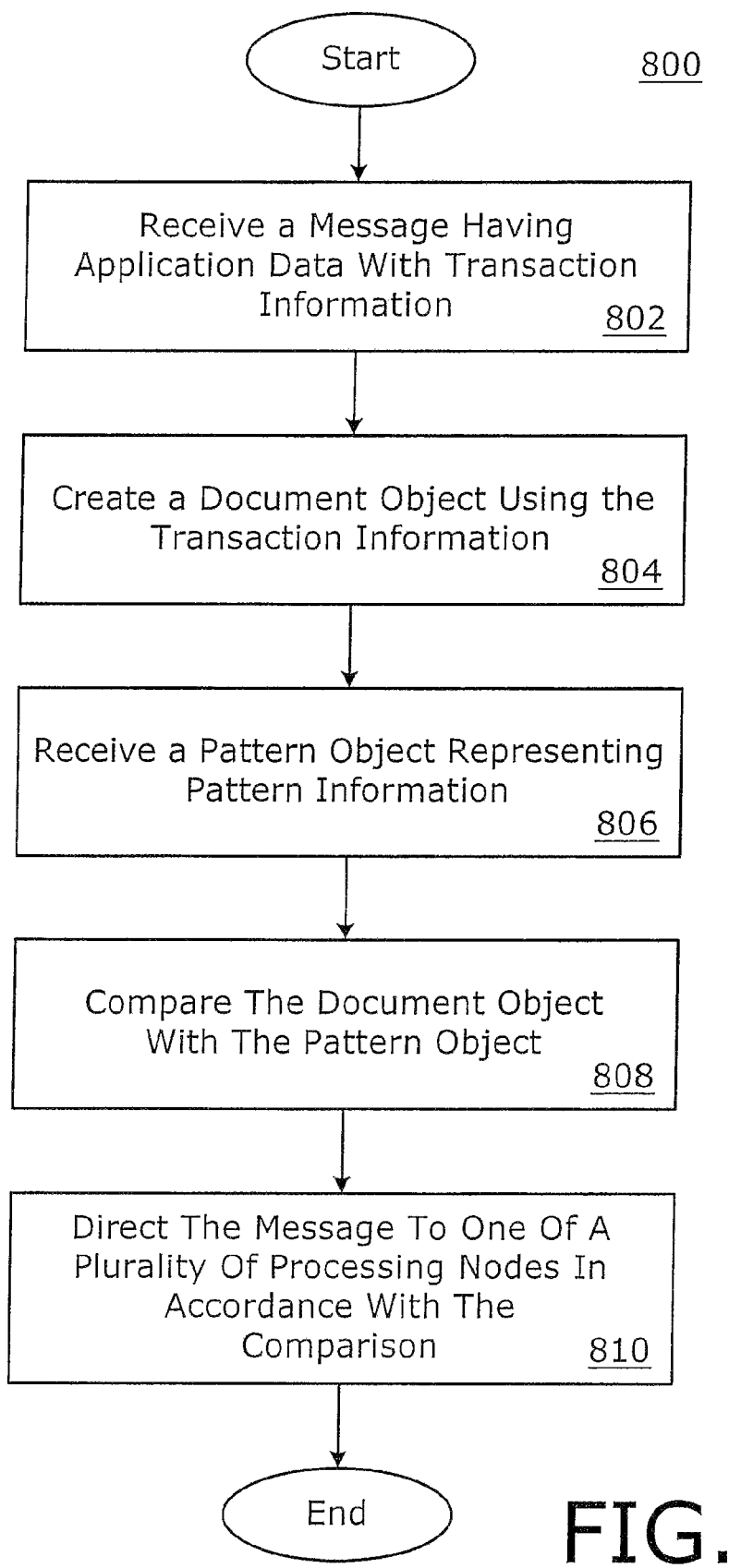

900 expr_t (generic XML expression object)
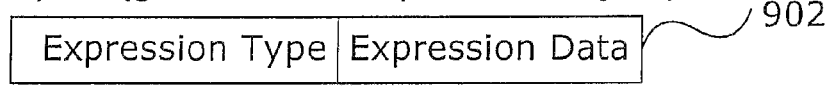
| Expression Type | Expression Data | 902

Bool_expr_t (comp_expr_t is similar) 904
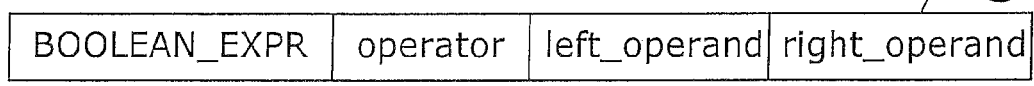
| BOOLEAN_EXPR | operator | left_operand | right_operand | path_t
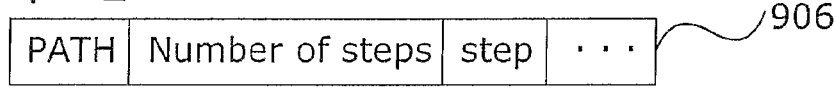
| PATH | Number of steps | step | ... | 906 step_t
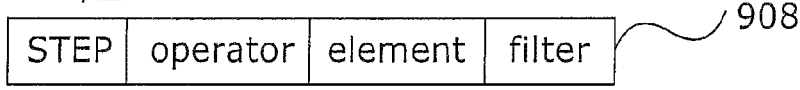
| STEP | operator | element | filter | 908 func_expr_t 910
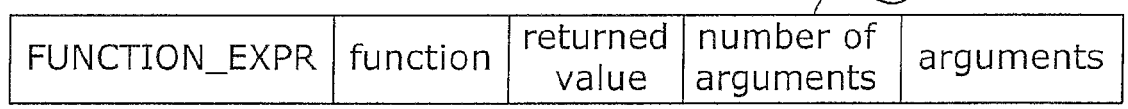
| FUNCTION_EXPR | function | returned value | number of arguments | arguments | element_t 912
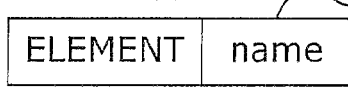
| ELEMENT | name | attribute_t
 914
| ATTRIBUTE | name | text_t 916
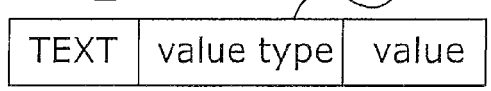
| TEXT | value type | value | default_t
 918
| DEFAULT |

FIG. 9

METHOD AND APPARATUS FOR CONTENT BASED SWITCHING

CROSS-REFERENCE TO RELATED APPLICATIONS

This application is a continuation of U.S. patent application Ser. No. 09/927,255 filed on Aug. 10, 2001 which issued as U.S. Pat. No. 7,096,270 on Aug. 22, 2006; which is a Continuation-In-Part of U.S. patent application Ser. No. 09/549,041 filed on Apr. 13, 2000 which issued as U.S. Pat. No. 6,732,175 on May 4, 2004.

BACKGROUND

Content based switching provides a way to offer different classes of service based on the content of a document. Content based switching operates to direct the document to a different network node based on information stored in the document. This may provide a way to tailor services to a particular document. For example, assume a data center comprises server A and server B, with server A providing information on cats and server B providing information on dogs. Content based switching technology may examine a document for the word "cat" or "dog," and route the document to server A or server B accordingly.

As with many network systems, content based switching may introduce some delay into a system. The amount of delay tolerated by a particular system may vary based upon various design goals. The delay introduce by content based switching may also vary depending on a number of factors. For example, a document may be relatively large. The larger the document, the more time it may take to search the document for a particular set of information, referred to herein as a pattern. Therefore, there may be a substantial need to increase the efficiency of content based switching to decrease latency to meet the design parameters for a particular system.

BRIEF DESCRIPTION OF THE DRAWINGS

The foregoing and a better understanding of the present invention will become apparent from the following detailed description of exemplary embodiments and the claims when read in connection with the accompanying drawings, all forming a part of the disclosure of this invention. While the foregoing and following written and illustrated disclosure focuses on disclosing example embodiments of the invention, it should be clearly understood that the same is by way of illustration and example only and is not limited thereto. The spirit and scope of the present invention is limited only by the terms of the appended claims.

The following represents brief descriptions of the drawings, wherein:

FIG. 8 is a block flow diagram of the programming logic performed by a director 145C in accordance with one embodiment of the invention.

FIG. 9 illustrates a data structure for a pattern object in accordance with one embodiment of the invention.

DETAILED DESCRIPTION

Figure 1:
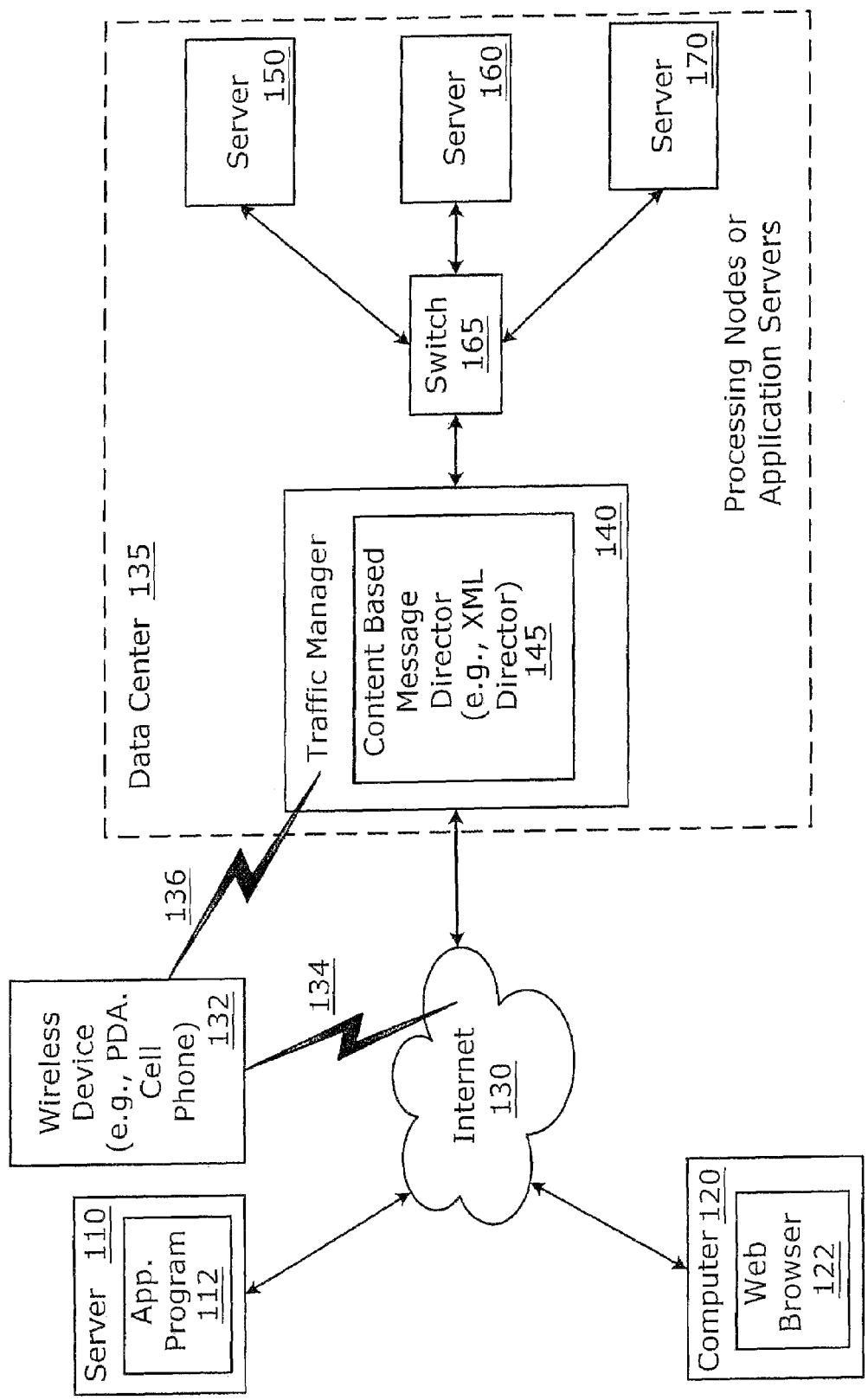
FIG. 1 is a block diagram of a network system according to an example embodiment.

While increasingly more successful in their roles as store and forward data systems, computer networks such as the Internet are experiencing tremendous growth as transaction-based, mission critical business applications, Web site owners, and business servers are overwhelmed by explosive traffic growth. The traditional approach is to buy more servers and network bandwidth. There is typically no distinction between levels of service, but rather a first-in first-out (FIFO) best efforts approach has been the default. However, this has resulted in uneven performance and undifferentiated service. Clearly, there is a need for a technique to allow service providers to intelligently offer different services and different levels of service depending on the circumstances.

Systems are available that allow messages to be routed based upon headers or header information. For example, in Hypertext Transfer Protocol (HTTP), a Post request method includes a request line, a header (or one or more headers) and a body. The request line includes a pointer to a requested resource or program to process the message, such as a Universal Resource Identifier (URI) or Universal Resource Locator (URL). The HTTP header may also include the type of message, the length of the body, and the date. There are systems that parse or examine the URL (i.e., the request line) and/or the HTTP header, and then route the message to a destination node based on the URL and/or header. One such system is described in "The Advantages of F5's HTTP Header Load Balancing Over Single-Point URL Parsing Solutions." However, this approach is very limited as switching decisions are based only on the HTTP header and/or URL.

Another system, known as BizTalk™, improves slightly on the URL parsing technique by providing a system that is compatible with XML-based messages.

XML, or eXtensible Markup Language v. 1.0 was adopted by the World Wide Web Consortium (W3C) on Feb. 10, 1998. XML provides a structured syntax for data exchange. XML is a markup language, like HTML. Most markup languages, like HTML, are fixed markup languages. That is, the fixed markup languages (including HTML) include a set of fixed tags for crafting a document. On the other hand, XML does not define a fixed set of tags, but rather, only defines a syntax or structured format through which users can define their own set of XML tags. There presently are a number of XML based languages that define their own set of tags using the XML syntax. XML has the further advantage because the actual data is separated from the presentation of the data, in contrast with HTML which combines these two items. As a result, XML has the potential to become a standard by which most computers, servers and applications will exchange or communicate data.

As described in "BizTalk Framework 1.0a Independent Document Specification," Microsoft Corp., Jan. 7, 2000, BizTalk defines a specific set of tags (or BizTags) within a message that are used to specify business document handling (p.7). A Biztalk server uses information contained in the Biztags to determine the correct transport-specific destination address(es). (pp. 9, 11). However, the tags used to mark up business transaction information within the message body are determined by the individual implementation. These implementation-specific tags (provided in the content or business transaction information of the message body) are not considered BizTags (p. 11).

There are a number of disadvantages to such an approach. The BizTalk system is very limited because it can route or switch messages based only upon header or introductory information, based upon the fixed set of the BizTalk tags. The BizTalk system does not make decisions or route/switch messages based upon the actual content or business information (e.g., business transaction information) within the message body. Moreover, to provide routing or address information, the Biztalk system requires that messages conform to the required format for the fixed set of Biztags, which is very inflexible and will likely inhibit the routing or switching of messages provided according to the other XML based languages (e.g., CXML, WML). Finally, many processing nodes, application servers and the like are presently burdened with a number of activities, such as establishing connections, communicating and processing requests for business related information, purchase orders, invoices or other business transactions. Further burdening a server with routing or switching decisions will require significant application processing cycles or bandwidth. This may overburden the server or negatively impact the server's ability to adequately handle business transactions.

According to an example embodiment, a network apparatus is provided between a network and a plurality of processing nodes (e.g. web servers, application servers, fulfillment servers, XML servers, routers, switches or other devices). The network apparatus includes a content based message director (e.g., a XML director) to route or direct messages received from the network to one of the processing nodes based upon the content of the application data in the message, including business transaction information. The application data (including business transaction information) may advantageously be provided as a XML based language.

The application data may be transmitted or received via a cell, packet or other envelope. The application data (such as business transaction information) is data to be processed by an application or program running on an application server, an XML server (which processes XML documents) or other processing node. Business transaction information can include a wide variety of application level information or transaction information such as purchase orders, invoices, inventory requests or replies, stock quotes, stock trade requests or confirmations, bids, transaction confirmations, shipping/delivery instructions or requests, materials or resource usage indications or measurements, information related to a transaction and its many details, etc.

According to one or more embodiments, the network apparatus includes many advantages. First, by examining well beyond a request line (e.g., URL) and message headers and into the content of the application data (such as the business transaction information) of a message, businesses can provide improved differentiation of services and different service levels for received requests and messages based upon the business transaction information in the messages. Second, by providing the content based message director (or XML director) as a network apparatus located between the network and one or more processing nodes or application servers, the burden of examining the application data or business transaction information and then switching to a particular processing node (e.g., performing XML switching) is offloaded from application servers to a network apparatus (e.g., network appliance, network processor, network server, or the like). Also, the content based message director (or XML director) can receive and switch messages based upon application data or business transaction information regardless of the transport or protocol used to transport the message (e.g., the director is transport independent). Finally, the XML director is not limited to receiving and processing XML data according to a set of fixed tags, but rather, is compatible with any of the XML based languages.

Referring to the Figures in which like numerals indicate like elements, FIG. 1 is a block diagram of a network system according to an example embodiment. As shown in FIG. 1, a variety of clients may be coupled or connected to a data center 135 via a network, such as the Internet 130. The clients, for example, may include a server 110 that includes an application program 112, a computer 120 (such as a personal computer or laptop) that may include a web browser 122 and a wireless device 132, such as a personal digital assistant (PDA) or a wireless (or cellular) telephone. Wireless device 132 may be coupled to the Internet 130 or to a data center 135 via communications links 134 and 136, respectively. Links 134 and 136 each may include one or more of a wireless link (e.g., cellular or other link) or a wireline link. Each of the clients, including server 110, computer 120 and device 132 can send and receive messages over the Internet 130 and may use a variety of different protocols or transports.

The data center 135 is provided for sending, receiving and processing a wide variety of messages, requests, business transactions, purchase orders, stock quotes or stock trades, and other information. The data center 135 includes several processing nodes (e.g., servers), including server 150, server 160 and server 170 for handling the various orders, business transactions and other requests. The different servers in data center 135 may be allocated to provide different services, or even different levels of services. According to an example embodiment, the clients and the data center 135 exchange business transaction information or other information by sending and receiving XML messages (data provided in XML or in a XML based language), or messages based upon another type of structured syntax for data interchange.

The various servers (e.g., servers 150, 160 and 170) are coupled to a traffic manager 140 via a switch 165. Traffic manager 140 may perform a variety of functions relating to the management of traffic, including load balancing (e.g., balancing the load of incoming messages or requests across the available servers according to some policy, such as round-robin, least number of connections, or other load balancing technique).

Referring to the clients again in FIG. 1, application program 112 may be a business program or a program for managing inventory, orders or other business transactions. For example, application program 112 may automatically and electronically detect that inventory has decreased below a threshold value and then automatically generate and send a purchase order to a supplier's server at data center 135 to request a shipment of additional supplies or inventory. Thus, server 110 may initiate, for example, a business-to-business (B2B) transaction by sending an electronic order to the supplier's remote server located at data center 135.

As another example, web browser 122 may request web pages, business information or other information from a remote server (e.g., located at data center 135). Web browser 122, may also send or post purchase orders, business transactions or other business information to a remote server, which may be located at data center 135. Wireless device 132 may receive information or data related to purchase orders, business transactions, web pages, stock quotes, game scores and the like from one or more remote servers (such as servers located at data center 135).

According to an embodiment, the server 110, computer 120 and wireless device 132 each may communicate or interchange data with one or more remote servers (e.g., servers 150, 160 and 170) by sending and receiving XML data (i.e., application data that is encoded or formatted according to the XML standard or according to one or more XML based languages).

According to an example embodiment, the traffic manager 140 includes a content based message director 145 to direct or switch messages to a selected server based upon the content of application data, such as business transaction information (which may be provided as XML data). Traffic manager 140 and/or message director 145 may be hardware or a combination of both hardware and software, and may even be provided on or as part of a network processor. It should be noted that director 145 may operate by itself, or as part of a larger network apparatus, such as part of a traffic manager 140.

According to an example embodiment, because of the advantages of XML, application data can advantageously exchanged between the servers of data center 135 and one or more clients or computing nodes by sending and receiving messages that include application data that is encoded or formatted according to the XML standard. Therefore, according to an embodiment, director 145 may be a XML director because it directs (or routes/switches) the incoming message to a particular server based upon the XML data in the message. The XML data preferably complies with the format or syntax required by the XML standard. A document that uses tag formats (e.g., start tags, end tags) and other syntax (e.g., to markup data) that complies with the XML standard is considered to be a "well-formed" XML document.

Therefore, in an exemplary embodiment, content based message director 145 is a XML director. However, it should be understood that director 145 can direct or switch messages having basically any type of structured syntax, including any type of markup language.

An advantageous aspect of the embodiment of the traffic manager 140 and director 145 shown in FIG. 1 is that the traffic manager 140 and the director 145 are located in front of the one or more application servers or processing nodes. By locating the traffic manager 140 and director 145 in a computer, server or computing system in front of the processing nodes or servers (as shown in FIG. 1) (e.g., coupled between the network 130 and the servers), the traffic management functionality and the functionality of the director 145 can be off-loaded from an application server to a separate and/or dedicated network apparatus or network system. This can advantageously relieve the processing nodes or application servers from this additional processing overhead.

Figure 2:
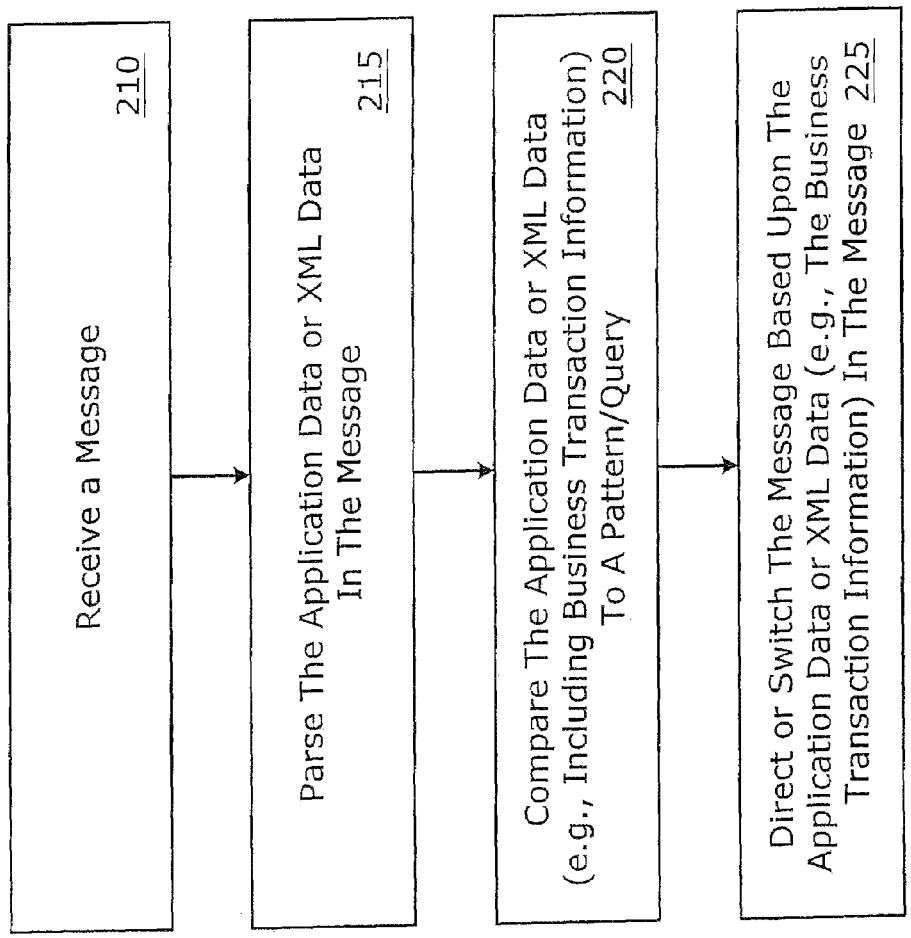
FIG. 2 is a flow chart illustrating an operation of content based message director according to an example embodiment.

FIG. 2 is a flow chart illustrating an operation of content based message director according to an example embodiment. At block 210, the director 145 receives a message. The message may be sent over any transport or protocol(s), such as Transmission Control Protocol (TCP), File Transfer Protocol (FTP), Simple Mail Transfer Protocol (SMTP), Wireless Application Protocol (WAP, which may be used to send and receive information with wireless devices), Hypertext Transfer Protocol (HTTP), etc. The general teachings and the operation of the invention are not dependent upon any particular transport or protocol, but rather are transport-independent.

A HTTP Post is an example of a message. The format for an HTTP Post message (or HTTP request) may be presented as:
   request-line (the URL); identifies a program for processing
      the message headers (0 or more)
   <blank line>
   body (the application data or the XML data; only for a
      POST)
Here's an example:
POST www;acme.com/purchasing/order.cgi HTTP/1.1
Content-Type: text/xml
Content-Length: 1230
User-Agent: Cern-Line Mode/2.15
Date: 3/27/00

```
<XML>
    <From>intel.com</From>
    <To>bookstore.com</To>
    <PurchaseBook>
        <ISBN>02013798233</ISBN>
        <PurchaseAmount> 98</PurchaseAmount>
    </PurchaseBook>
</XML>
```

In this example, the URL (or request line) is provided in a request line to identify a program or application to process the message. Several header lines (Content-type, Content-length, date, etc.) make up an HTTP header. The application data is provided after the HTTP header, and in this example is provided as XML data. A start tag <XML>, and </XML>, an end tag, identify the start and end, respectively, of the application data (or XML data). This XML application data is also referred to as a XML document. The XML document includes markup characters (or tags) which describe data, and data characters. As an example, a "To" element of the above XML document is written as: <To>bookstore.com</To>. Where<To> is a start Tag and </To> is an end tag, which are markup characters because they describe the XML data characters (bookstore.com). The business transaction information describes the business transaction (To, From, items purchased, purchase amount, quantity, etc.), and is not included in the URL, the HTTP header, or any other header (e.g., IP header, TCP header) of the envelope used for sending the message.

While the prior art performed switching based on the request line or URL and/or the HTTP header, the present invention is directed to a technique to perform switching at a network apparatus based upon the application data, such as XML data (which includes business transaction information).

In this example message, the business transaction information provided within the application data as XML data relates to the transaction or describes the transaction, including, for example, what kind of business transaction (a purchase order or to purchase a book), who it is from and who it is to, an ISBN number to identify the goods to be purchased and the amount of the purchase (PurchaseAmount). These are merely examples of the types of business transaction information in a message upon which the director 145 can analyze and make routing or switching decisions for the message.

At block 215 of FIG. 2, the director 145 (FIG. 1) parses all or part of the application data (the XML data in this example) and can check to ensure that the XML document or application data is well formed (i.e., checks to make sure at least a portion of the XML document meets the so-called well-formedness constraints or requirements in the XML specification or standard). Parsing generally refers to the process of categorizing the characters or XML data that make up the XML document as either markup (e.g., <To>) or character data (e.g., bookstore.com).

At block 220 of FIG. 2, the application data or XML data (including markup characters and/or character data) is then compared to one or more configuration patterns or queries (which may be stored in the director 145) to determine if there is a match. According to an embodiment, the configuration patterns may be dynamically changed or updated by a user or by a program or application. For example, a program may detect the failure of one or more servers and/or detect the response time of servers, and then update the configuration pattern to account for these changes in the network (e.g., redirect certain messages from busy servers to servers which are less busy, or from servers which have failed to the available servers).

At block 225, if there is a match between the content of the application data (e.g., the business transaction information which may be provided as XML data) of a message and a configuration pattern or query, then the director 145 directs or switches the message to the corresponding server (or processing node) in the data center (e.g., directed to the specific server as indicated by the configuration pattern). If there are multiple matches, the director 145 can just direct the message based to the first match, or a load balancing policy can be used to balance messages among a group of servers. If there is no match, the message can be directed to a default server or can be blocked. Alternatively, the configuration pattern can also identify a certain pattern for which a message should be blocked from being forwarded. In this respect, the director 145 may also act as a filter to selectively pass or forward some messages while blocking others, based upon the application data.

For example, the director 145 may be configured to direct or switch messages based on the following configuration patterns or queries:

| Server | IP address | Port | XML pattern |
|---|---|---|---|
| S1 (e.g., 150) | 10.1.1.1 | 80 | To = bookstore.com |
| S2 (e.g., 160) | 10.1.1.2 | 80 | To = stockquote.com |
| S3 (e.g., 170) | 10.1.1.3 | 80 | To = computerstore.com |

Based on the above configuration patterns, the director 145 would direct a message to server S1 (having the IP address 10.1.1.1 and port 80) if the data for the To element of the business transaction information is bookstore.com. The message will be directed to server S2 (having an IP address 10.1.1.2 and port 80) if the data for the To element of the business transaction information is stockquote.com. And, the director 145 will direct any messages to server S3 if the data for the To element of the business transaction information is computerstore.com.

This advantageously allows different types of services (or different levels of service) to be provided for messages based on the content of the application data (such as the business transaction information) in the message. In this example, server S1 may be allocated to handle purchase orders for books sent to bookstore.com. Server S2 may be allocated to process requests for real-time stock quotes, while server S3 may be allocated to process purchase orders for computers sent to computerstore.com.

There are many examples where content based switching based upon the content of the application data or business transaction information can be used to offer different or differentiated services or even different or differentiated levels of services. As another example, the director 145 may be configured to direct or switch messages based on the following configuration patterns or queries:

| Server | IP address | Port | XML pattern |
|---|---|---|---|
| S1 (e.g., 150) | 10.1.1.1 | 80 | PurchaseAmount < $100 |
| S2 (e.g., 160) | 10.1.1.2 | 80 | $100 < PurchaseAmount < $1000 |
| S3 (e.g., 170) | 10.1.1.3 | 80 | $1000 < PurchaseAmount |
| S4 (not shown) | 10.1.1.4 | 80 | $1000 < PurchaseAmount |

In this example, messages for purchase orders are sent to server S1 if the purchase amount is less than $100; messages for purchase orders are sent to S2 if the purchase amount is less than $1000 and more than $100; and for the high dollar purchases, the messages for purchase orders for purchases greater than $1000 can be sent to either of two servers. In this fashion, the director 145 (FIG. 1) can direct or route received messages based on the content of the application data or business transaction information in the message. This allows web sites or electronic-businesses (e-businesses) to offer different or differentiated levels of services based on the content of the application data or transaction information.

In this particular example, two servers (S3 and S4) have been allocated to handle the highest dollar purchase orders. Thus, by specifically allocating greater resources (e.g., two or more servers as compared to just one server) for the higher dollar amount purchases as compared to the lower dollar purchases, an e-business operating at data center 135 can provide a higher level of service for purchase order messages having a higher dollar purchase amount. In this manner, director 145 can switch or direct messages to another network device or to a specific server based upon a wide variety of business transaction information or application data.

Figure 3:
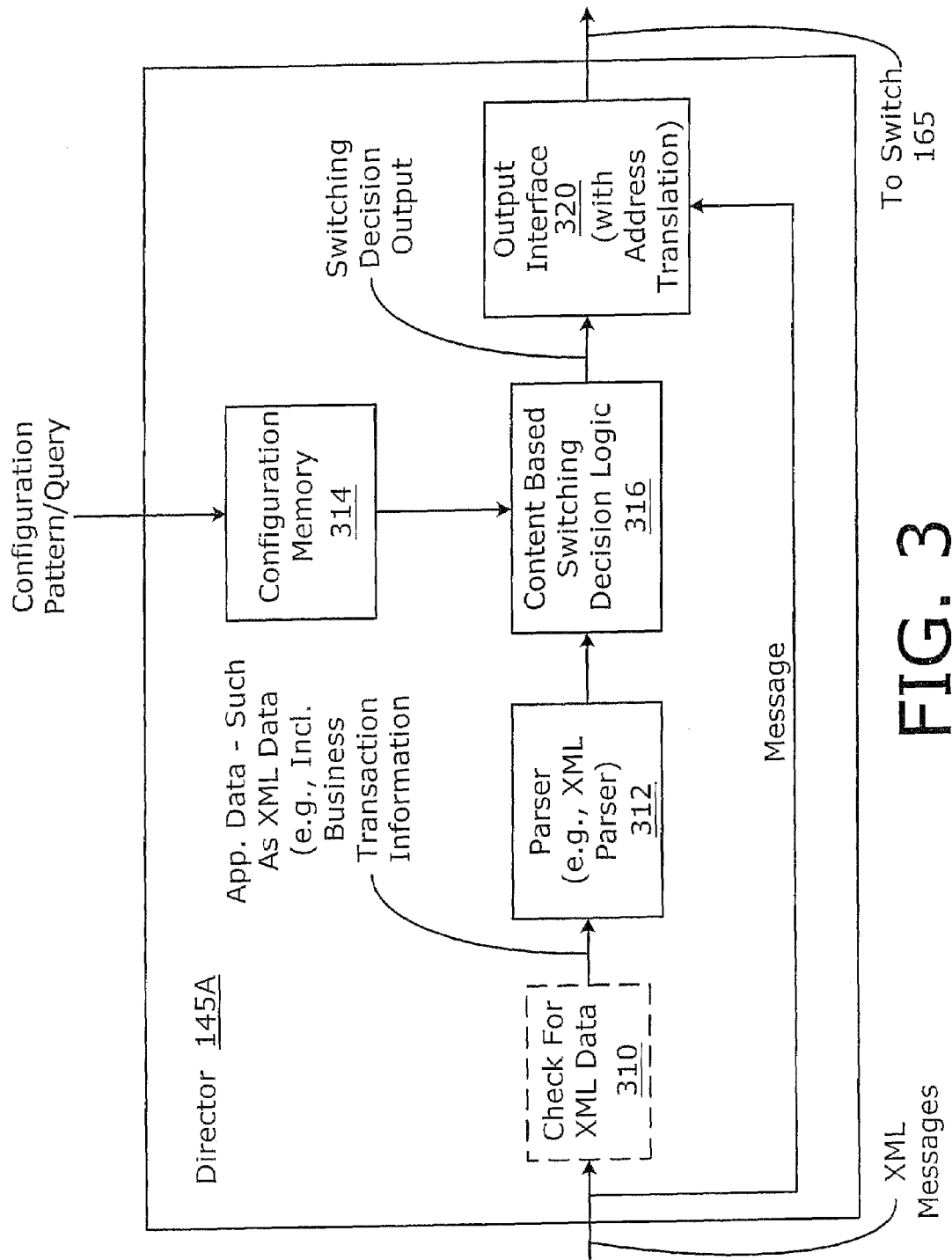
FIG. 3 is a block diagram illustrating a director according to an example embodiment.

FIG. 3 is a block diagram illustrating a director according to an example embodiment. Director 145A includes a block 310 to determine whether a received message includes XML data.

According to an embodiment, if the message does not include XML data, the message will be passed (e.g., directly) through to the output with little if any further processing by director 145A. If the message does include XML data, then the message will be analyzed for making a routing or switching decision as described below.

There are many ways in which block 310 can determine whether a received message includes XML data. According to one embodiment, certain types of filenames (e.g., invoice.cgi) or filename extensions (e.g., *.cgi), which may typically be provided in the request line, may indicate whether the message includes XML data. Thus, the filename extension may be analyzed by block 310 to determine whether the message includes XML data. Other information in the message, including other header information or even a particular tag in the application data itself (e.g., the <XML> start tag) can be used to identify whether or not the message includes XML data.

According to an embodiment, block 310 is optional. However, it is advantageous to provide block 310 where only a small percentage of the incoming messages include XML data. Without block 310, application data for all messages will be parsed and compared to the configuration pattern, and a switching decision will be generated. Thus, for those messages which do not include XML data (and thus cannot be switched or directed by director 145A), director 145A will add unnecessary latency in the message forwarding path in the absence of block 310. On the other hand, where a significant percentage of the messages received by director 145A include XML data, block 310 may be considered unnecessary and may be omitted (because block 310 would typically add unnecessary latency in such case).

A parser 312 is coupled to the output of the block 310 to parse the application data (or a portion thereof). A configuration memory 314 receives and stores one or more configuration patterns or queries. A content based switching decision logic 316 receives the output from the parser 312 and compares the configuration patterns to the application data or business transaction information (e.g., including the data and the markup characters describing the data within the configuration pattern). The content based switching decision logic 316 then outputs a switching or routing decision for the message on the basis of the comparison (i.e., on the basis of the business transaction information). The configuration pattern may indicate both a pattern and a processing node or server to process the message if a pattern is found in the message.

The output interface 320 then switches or directs the message on the basis of this decision (e.g., routes the message to the processing node or server indicated by the matching configuration pattern). For example, if there is no match, the output interface 320 may filter or block the message, or may direct or route the message to a default server or a predetermined server in the data center 135. If a match is found, the output interface 320 switches or directs the message to the appropriate destination (e.g., to the appropriate processing node or server within data center 135).

The configuration pattern may require multiple patterns, or even a hierarchical arrangement of data elements in the application data for a specific match. For example, the decision logic 316 may receive a configuration pattern that specifies:

| Server | IP address | XML pattern |
|---|---|---|
| S1 (e.g., 150) | 10.1.1.1 | From = Intel; and PurchaseAmount < $100 |

In such a case, the switching decision logic 316 would examine the application data (or XML data) to first identify a From tag that is set to Intel. Next, it would examine the transaction information to identify a PurchaseAmount that is less than $100. If both of these are found, this indicates a match.

If a match is found between the business transaction information and the pattern, the content based switching logic 316 outputs a switching decision to a output interface 320. The switching decision may, for example, indicate that a match was found and identify the processing node or server (e.g., by address and port number or other identifier) where the message should be directed.

According to an example embodiment, the decision logic 316 provides an IP address and port number to be used as a new destination IP address and destination port number for the message. The output interface 320 may then translate the destination IP address and port number in the packet or envelope of the received message from the original destination IP address and port number (i.e., the IP address and port number of the traffic manager 140 or director 145A) to the new destination IP address and port number provided by the decision logic 316. According to an embodiment, the new destination IP address identifies a processing node or server (e.g., within data center 135 or elsewhere) and the new destination port number identifies a program or application on that processing node or server that will receive and process the message.

The message (e.g., with its associated TCP and IP headers translated or modified to include the new destination address and port number) is then output from the director 145 and traffic manager 140. Switch 165 receives the message, and then routes the message to the appropriate processing node or server based on the IP address.

According to an example embodiment, a client (e.g., a server 110, computer 120, etc., FIG. 1) that sends a message first establishes a connection (e.g., a TCP connection), and then sends the message via HTTP (or other transport) to the traffic manager 140 and/or director 145A. The director 145A then parses the XML data, and makes a switching decision based on the business transaction information in the message as compared to one or more configuration patterns. A new connection is then established between the director 145A or traffic manager 140 and the destination processing node or server. The message is then directed or routed from director 145A to the specified node or server.

Figure 4:
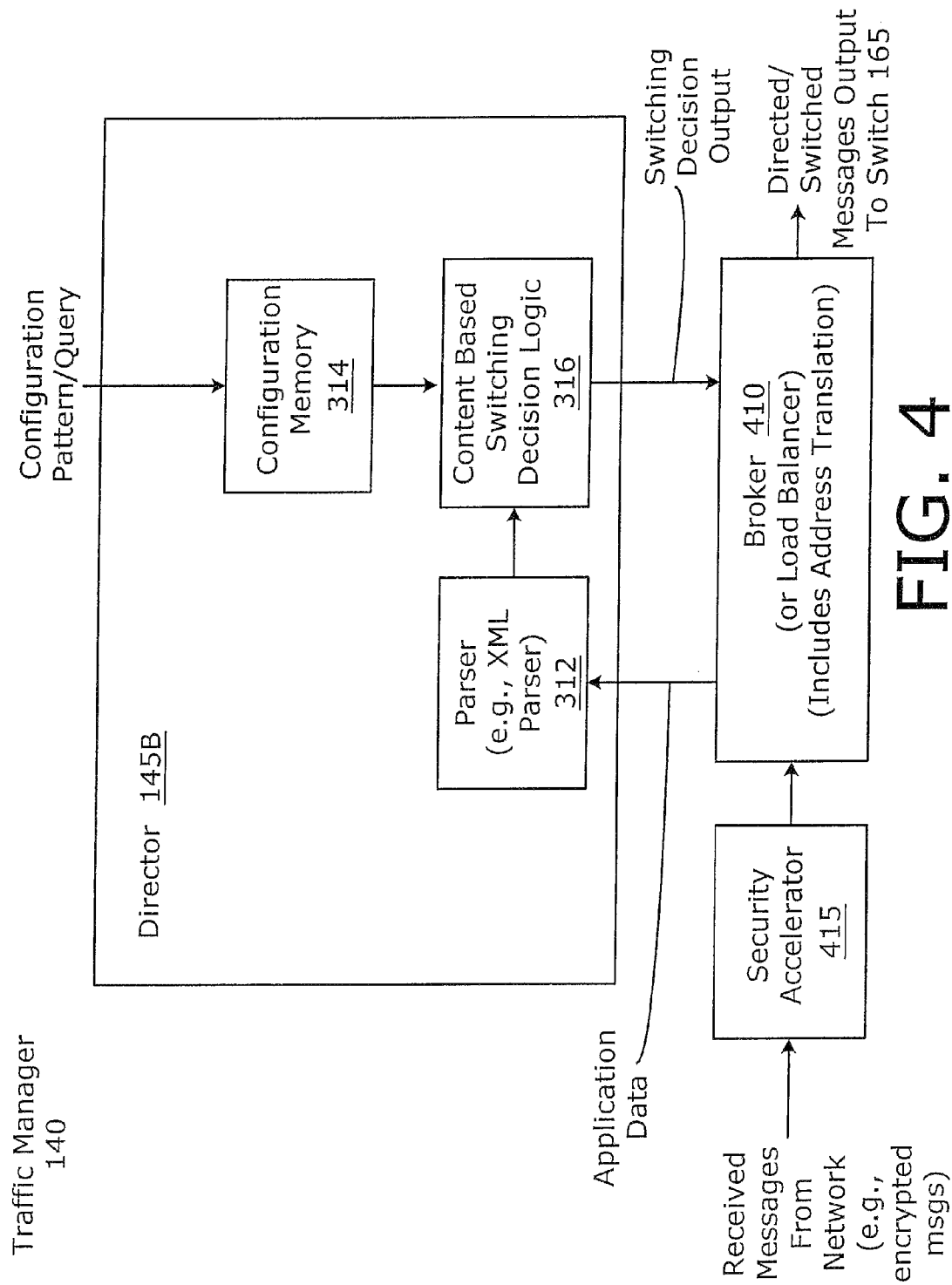
FIG. 4 is a block diagram illustrating a traffic manager according to another example embodiment.

FIG. 4 is a block diagram illustrating a traffic manager according to another example embodiment. Traffic manager 140 includes a security accelerator 415 for encrypting outgoing messages and/or decrypting incoming messages received from the network. According to an embodiment, the security accelerator 415 is a Secure Sockets Layer (SSL) accelerator, available from Intel Corporation. The security accelerator 415 allows the security related tasks such as encryption and/or decryption to be off-loaded from the application server to the accelerator 415 of the traffic manager 140.

Traffic manager 140 also includes a director 145B and a broker 410. A decrypted message is received by broker 410 from security accelerator 415. According to an example embodiment, broker 410 operates as both an output interface (similar to output interface 320) and a load balancer to balance or adjust the traffic between one or more of servers or processing nodes within the data center 135.

Director 145B is similar to director 145A but may not include block 310 and/or the output interface 320 of director 145A (as these functions may be provided by the broker 410 in FIG. 4). Parser 312 (which may be optional) parses the XML data. The content based switching decision logic 316 compares the configuration patterns to the application data or business transaction information in the message and then outputs a switching decision to broker 410 for the message on the basis of the comparison. The switching decision output to broker 410 may, for example, identify the IP address and port number of the selected processing node or server or application server that should receive the message.

Broker 410 performs address translation on the header(s) for the message. The address translation performed by broker 410 includes a destination address and destination port translation and an optional source address and source port translation. The destination address and port translation may be performed by translating the original destination IP address and port number of the received message (which may identify the broker 410) to the IP address and port number of the specified processing node or server (or of the specified server resource or program). In addition, the broker may also translate the source IP address and port number in the packet or envelope from the originating client's address and port number to the IP address and port number of the broker 410 (or of the traffic manager 140). The message (including one or more translated addresses) is then output from broker 410. Switch 165 (FIG. 1) receives the message and forwards the message to the appropriate server based on the destination address in the message. According to one embodiment, it is not necessary to actually translate the source IP address and port number if all return messages or replies from the processing node or server are routed through the broker 410.

Broker 410 also translates destination addresses for return messages or replies from the processing node or server sent to the client, to substitute the IP address and port number of the client as the destination address and port for the return message or reply. Thus, the broker 410 may operate as a gateway or output interface between the client (FIG. 1) and the processing node or server, by performing destination address translation prior to routing or forwarding the message, and performing a similar translation for return or reply messages sent from the processing node or server back to the client.

According to an example embodiment, broker 410 and security accelerator 415 may be provided, for example, as an Intel® NetStructure™ 7180 E-Commerce Director. Alternatively, the broker 410 may be provided as an Intel® NetStructure™ 7170 Traffic Director. Both are available from Intel Corporation, Santa Clara Calif. As a result, broker 410 may perform additional functions including load balancing according to a load balancing policy or algorithm to adjust the load on each server in the data center.

Figure 6:
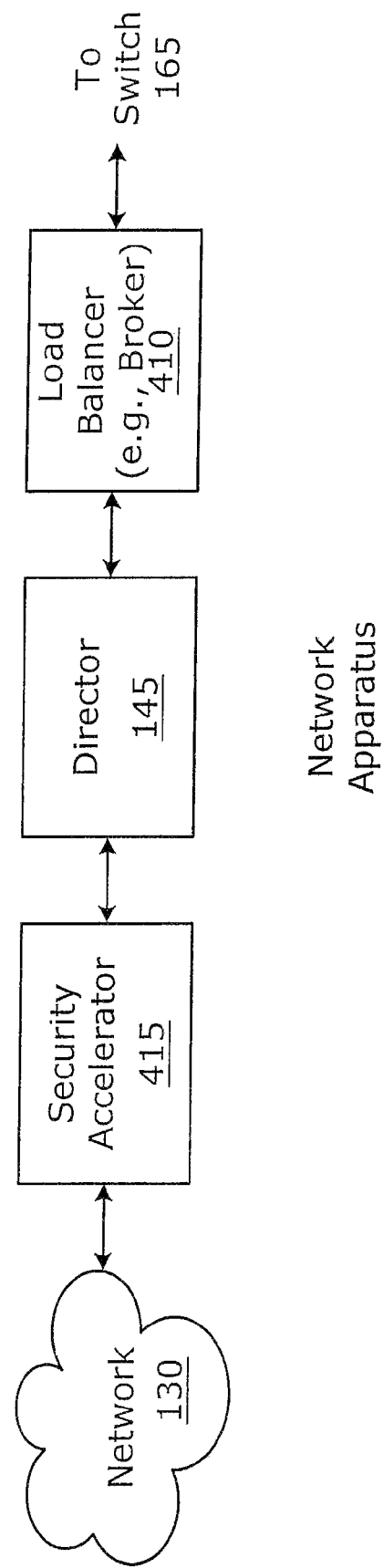
FIG. 6 is a block diagram illustrating a network apparatus according to another example embodiment.

The director 145 (or 145A or B), the security accelerator 415 and the broker 410 (or load balancer) may be provided in a network apparatus in different combinations, depending on the circumstances. FIG. 6 is a block diagram illustrating a network apparatus according to another example embodiment. For example, each of the director 145, security accelerator 415 or load balancer (or broker 410) may be provided by itself. Alternatively, all three of the security accelerator 415, an XML director 145 and a load balancer may be provided within a network apparatus or traffic manager, as shown in FIG. 6. Or, the XML director 145 may be combined with just one of either a security accelerator 415 or a load balancer (broker 410). Other combinations are possible.

Figure 5:
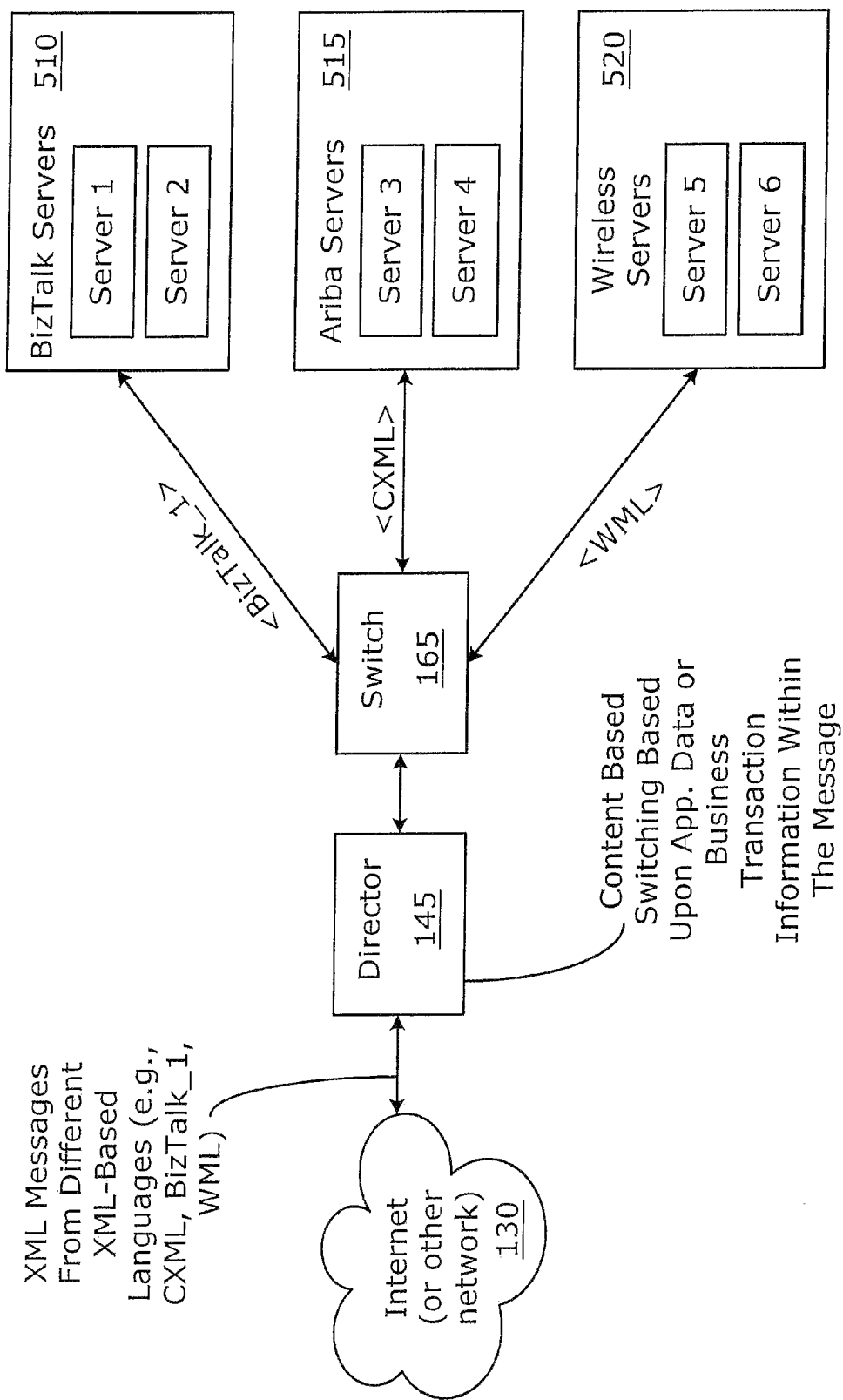
FIG. 5 is a block diagram illustrating another example operating environment for a content based message director according to an example embodiment.

FIG. 5 is a block diagram illustrating another example operating environment for a content based message director 145 according to an example embodiment. As noted above, XML does not define a fixed set of tags, but rather, only defines a syntax or structured format through which users can define their own set of tags or their own XML based language. In fact there are many different XML-based languages in use, each having a unique set of tags that define what elements should be provided to comply with that XML language.

An XML language is defined by a validation template (indicating the proper form for the tags), known in XML as a Document Type Definition (DTD). For example, BizTalk by Microsoft Corp. includes one set of XML tags; CXML by Ariba Corp. includes its own set of tags; CBL by Commerce One includes another set of XML tags; While WML (Wireless Markup Language) defines yet another set of XML tags for the communication or interchange of data to and from a wireless device. Each of these XML-based languages includes a different or unique set of tags, and thus each is generally incompatible with the other languages. For example, a client sending data using CXML will not be able to properly communicate with a processing node or server that expects to receive data only provided according to WML.

According to an advantageous aspect of the present invention, director 145 can receive an XML message, compare the application data or business transaction information to the configuration pattern, and then direct or route the message (or make switching or routing decisions) to an appropriate processing node or server regardless of the type of XML-based language used by the message. Once the director 145 is configured to detect or recognize one or more specific tags and corresponding data (e.g., PurchaseAmount >$100), the director 145 can direct or route the message based on the content of the application data (e.g., based on the business transaction information provided as XML data), regardless of the type of XML-based language that is used by the message.

As shown in FIG. 5, Director 145 is coupled to switch 165. There are three sets of servers (or data centers) coupled to the switch 165, including: a set of BizTalk servers 510 (including servers 1 and 2) which communicate data using an XML based language known as BizTalk; a set of Ariba servers 515 (including servers 3 and 4) which communicate data using the XML based language known as CXML; and a set of wireless servers 520 (including servers 5 and 6) which communicate data using only the XML based language known as Wireless Markup Language or WML. These are merely provided as examples. Thus, the director 145 can operate as a gateway or interface, receiving messages from a variety of different clients using a variety of different XML based languages, and then directing or routing the messages to the appropriate processing node or servers.

Figure 7:
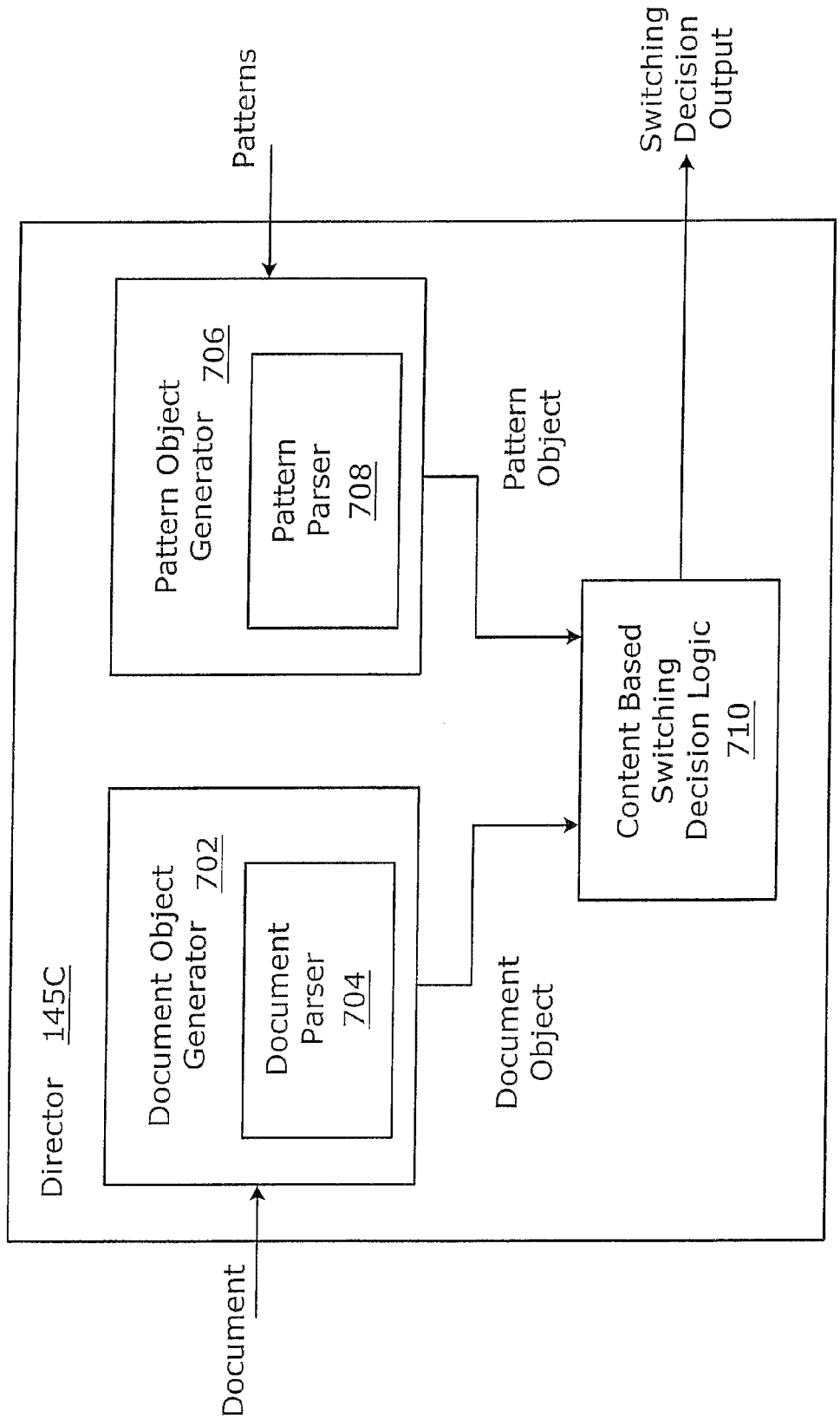
FIG. 7 is a block diagram illustrating a director 145C according to an example embodiment.

FIG. 7 is a block diagram illustrating a director 145C according to an example embodiment. Director 145C may comprise a document object generator 702, a pattern object generator 706 and a content based switching decision logic 710. Document object generator 702 may include a document parser 704. Pattern object generator 706 may include a pattern parser 708. In this embodiment, director 145C does not include a block 310 to determine whether a received message includes XML data, although director 145C may include block 310 and still fall within the scope of the invention.

As stated previously, director 145C may perform pattern matching against any documents having a structured syntax, such as an XML document. Director 145C accepts and XML document and one or more XML patterns and their associated user data. Director 145C matches the XML document against the list of XML patterns. In this embodiment of the invention, director 145C matches the XML document against one pattern at a time, although the matching may be performed against multiple patterns in parallel with the appropriate hardware resources. If a match is found, the user data associated with the matched XML pattern and/or the matched XML pattern are returned. The user data associated with an XML pattern may be an opaque object to director 145C and may be used to determine what action(s) are to be performed upon a match on a specific XML pattern, as discussed previously. The engine may be alternatively invoked with matching against all XML patterns specified. It is worthy to note that although some embodiments of the invention may be described using XML, it can be appreciated that any structured syntax may be implemented and still fall within the scope of the invention.

Director 145C may receive a document such as an XML document, although the embodiments of the invention are not limited in this context. The XML document may be passed to document object generator 702. Document object generator 702 may include a document parser 704 to parse the XML document into an XML object. An XML object is a data structure used to represent a logical tree of the XML document, as discussed in more detail with reference to FIG. 11. In one embodiment of the invention, only entities desired for the pattern matching process are stored in the data structure. Data on entities such as DTD, comments and processing instructions (PI) are not stored.

Well-formedness of the XML document may be implicitly checked when parsed by an XML parser (e.g., document parser 704). In one embodiment of the invention, an XML document that is not well-formed may be rejected. Various actions may be taken with rejected documents, including switching to a default server, dropping from the system, sending a message to the document owner informing them of the document status, and so forth.

Director 145C may also receive one or more patterns. The patterns may be passed to pattern object generator 706. Pattern object generator 706 may validate the syntax of the patterns, and create a pattern object for each pattern, as discussed in more detail below with reference to FIGS. 9 and 10. Pattern object generator 706 may include pattern parser 708 to parse a pattern in real-time. Alternatively, pre-parsed patterns may be stored in a memory (e.g., configuration memory 314) and made available to content based switching logic 710 to reduce the overhead of pattern parsing.

Director 145C may pass the document object and the pattern object(s) into content based switching decision logic 710. Content based switching decision logic 710 may perform pattern matching to determine whether a document matches one or more patterns. In one embodiment of the invention, director 145C is configured to traverse a document only until one or more patterns are matched to accelerate the pattern matching process. Alternatively, director 145C may traverse the entire document in accordance with a particular design goal. If a match is found, the user data associated with the matched XML pattern and/or the matched XML pattern are returned. The user data associated with an XML pattern may be an opaque object to director 145C and may be used to determine what action(s) are to be performed upon a match on a specific XML pattern. Examples of possible actions include those described previously as well as others.

FIG. 8 is a block flow diagram of the programming logic performed by a director 145C in accordance with one embodiment of the invention. Although the programming logic may be presented here in a particular sequence, it can be appreciated that the programming logic may be performed in any sequence and still fall within the scope of the invention.

FIG. 8 illustrates a programming logic 800. Programming logic 800 may include receiving a message having application data with transaction information at block 802. A document object may be created using the transaction information at block 804. A pattern object representing pattern information may be received at block 806. The document object may be compared with the pattern object at block 808. The message may be directed to one of a plurality of processing nodes at block 810 in accordance with the results of the comparison at block 808.

FIG. 9 illustrates a data structure for a pattern object in accordance with one embodiment of the invention. A pattern object may be a data structure that represents a pattern, such as an XML pattern. For example, an XML pattern may be represented by a number of sub-expressions, each represented by a separate XML expression object. FIG. 9 illustrates a set of XML expression objects, each containing an expression type and expression data. In one embodiment of the invention, a sub-expression may be referred to as a "PATH" expression that comprises one or more "STEPS," with each STEP representing a step within a PATH pattern.

As shown in FIG. 9, a pattern object data structure 900 may comprise blocks 902 to 918, with each block representing a predefined set of data. Block 902 may represent an expression block having a field for expression data. Block 904 may represent a Boolean expression, having fields for an operator, a left operand and a right operand. Block 906 may represent a PATH sub-expression, having fields for a number of steps and the step names and/or pointers. Block 910 may represent a function expression, having fields for a function name, a returned value, a number of arguments, and the argument(s). Block 912 may represent an element, having a field for an element name. Block 914 may represent an attribute, having a field for an attribute name. Block 916 may represent text, having fields for a value type and a value. Block 918 may represent default information. It can be appreciated that the pattern object data structure is not limited to these particular blocks or fields.

Figure 10:
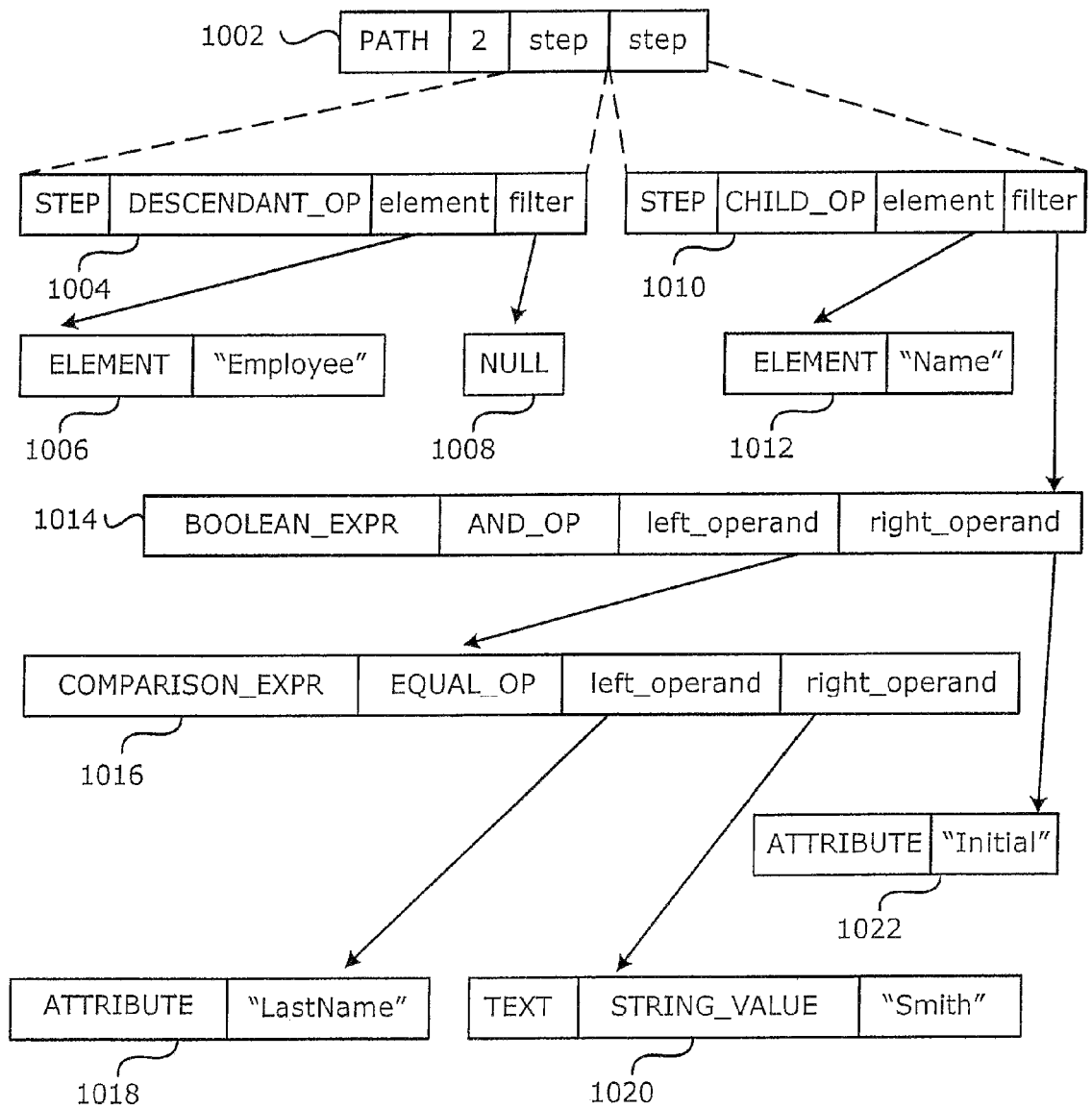
FIG. 10 provides an example of an XML pattern object in accordance with one embodiment of the invention.

FIG. 10 provides an example of an XML pattern object in accordance with one embodiment of the invention. Assume that pattern object generator 706 receives a new configuration pattern. The new configuration pattern is designed to find matches for employees having a last name of "Smith" and having an initial. Pattern object generator 706 would pass the pattern information to pattern parser 708 to parse the pattern in accordance with a pattern object data structure as described with reference to FIG. 9. Pattern parser 708 may receive a string of information written in a particular syntax or format, such as "employee last name=smith." Pattern parser 708 would parse the information string for individual elements, and place those elements in the appropriate block within the pattern object data structure. For example, pattern parser 708 may interpret the information string "employee last name=smith" as a PATH sub-expression 1002 having two steps 1004 and 1010. Step 1004 may represent a DESCENDANT_OP, having the element field set to "employee" and the filter field set to a NULL value (e.g., 0). Step 1010 may represent a CHILD_OP, having the element field set to "name" and the filter field set to a Boolean expression block 1014. The designators DESCENDANT_OP and CHILD_OP may indicate the order in which the XML pattern data structure is to be traversed during the pattern matching process. Boolean expression block 1014 may represent an AND_OP, with the left operand set to a comparison expression block 1016, and the right operand set to an attribute expression block 1022. Comparison expression block 1016 may represent an EQUAL_OP, with the left operand set to an attribute block 1018, and the right operand set to a text block 1020. Attribute block 1018 may have the attribute field set to "lastname." Text block 1020 may have the text field set to "smith" and the value "string_value" set to a value representing the length for the text field.

By having a configuration pattern parsed into a predefined pattern object data structure, content based switching decision logic 710 may use a pattern matching algorithm that is optimized to search for a particular set of pattern information within a document. Similarly, by having the relevant information from a document parsed into a document data structure, content based switching decision logic 710 may optimize matching the pattern information contained in the pattern object data structure with the document data stored in the predefined document object data structure.

Director 145C may receive a document (e.g., an XML document), and pass the document to document object generator 702. Document object generator 702 may pass the document to document parser 704 to parse the document into a document object (e.g., an XML document object). Document parser 704 may parse a predefined element node in the XML document as an entry in an XML document object. An element node as defined herein may be a block of information within a document, as determined according to a particular syntax or structure of the document.

The XML document object may have a data structure represented as a table similar to Table 1, with each row containing information about each element node. The XML document object may represent a logical semi-tree structure of the XML document tree as shown in TABLE 1 as follows:

TABLE 1

| Level | Element | Attribute List | Text | Child | Sibling |
|-------|---------|----------------|------|-------|---------|
| Level | Element | Attribute List | Text | Child | Sibling |
| ... | ... | ... | ... | ... | ... |
| ... | ... | ... | ... | ... | ... |
| ... | ... | ... | ... | ... | ... |

For a complete tree, each parent typically contains links to all its immediate children. In one embodiment of the invention, the document object contains only a link to the first child, with each child containing a link to its next sibling. To access all children, therefore, a parent may follow the child link, and then the sibling link of the child. This may be illustrated in FIG. 11.

Figure 11:
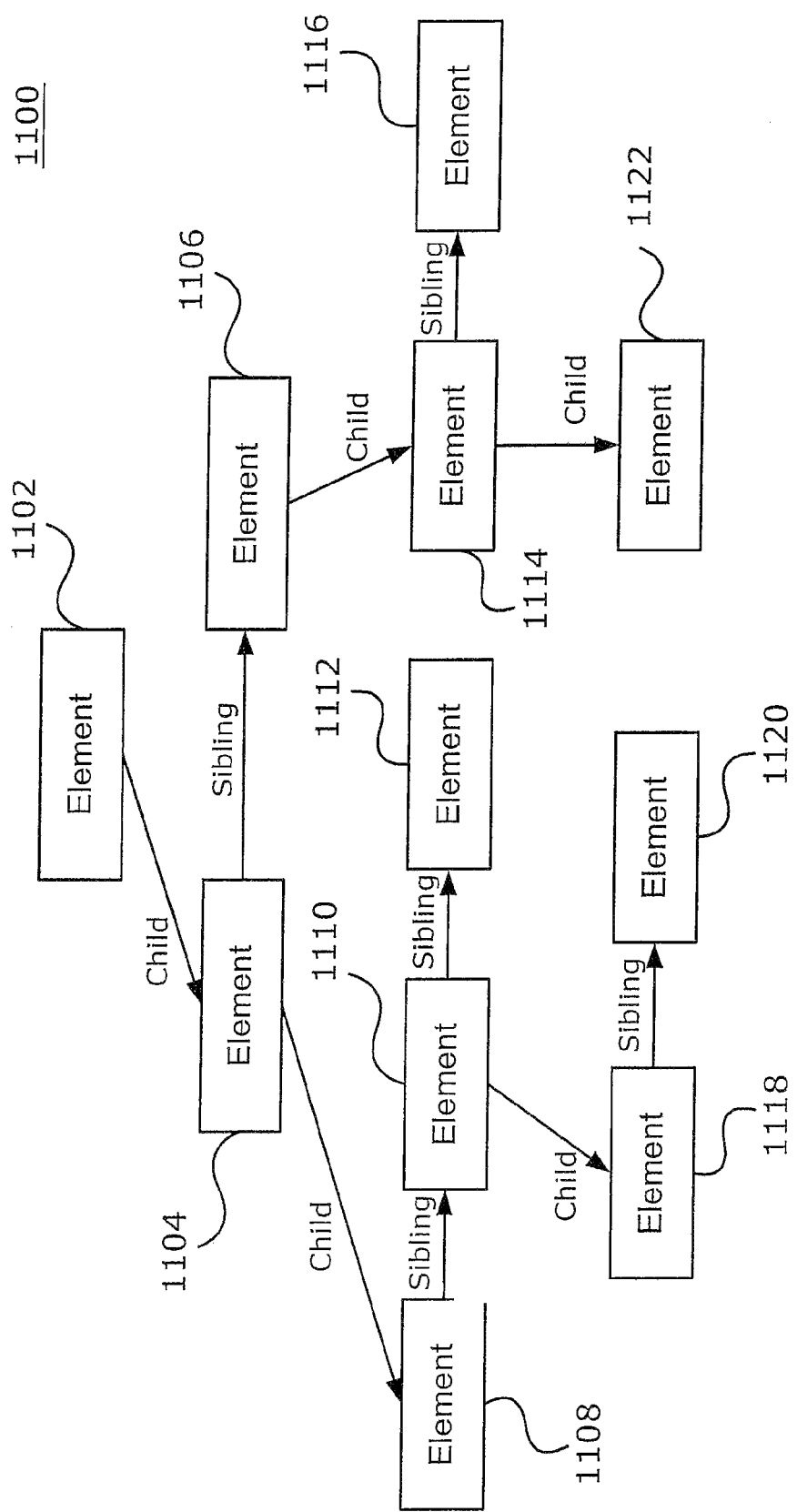
FIG. 11 illustrates a semi-tree structure represented by a document object in accordance with one embodiment of the invention.

FIG. 11 illustrates a semi-tree structure represented by a document object in accordance with one embodiment of the invention. FIG. 11 illustrates a logical semi-tree structure 1100 having elements 1102, 1104, 1106, 1108, 1110, 1112, 1114, 1116, 1118, 1120 and 1122. To traverse structure 1100, a program may start with 1102 and follow the relevant pointers to the desired element. For example, to retrieve element 1112, a program may traverse elements 1102, 1105, 1108 and 1110. By way of contrast, a normal tree structure may have a pointer for element 1104 directly to element 1112. Although this may potentially decrease search times, it also may increase the size of the data structure thereby increasing memory and processing requirements.

As discussed with reference to FIG. 8, the document object from document object generator 702 and the pattern object from pattern object generator 706 may both be passed to content based switching decision logic 710. Content based switching decision logic 710 may compare the document object with the pattern object to find a match(es). The comparison may be made using a pattern-matching algorithm optimized to use document objects and pattern objects. One embodiment of the invention utilizes a pattern-matching algorithm as described below, although the embodiments of the invention are not limited in this context.

Figure 12:
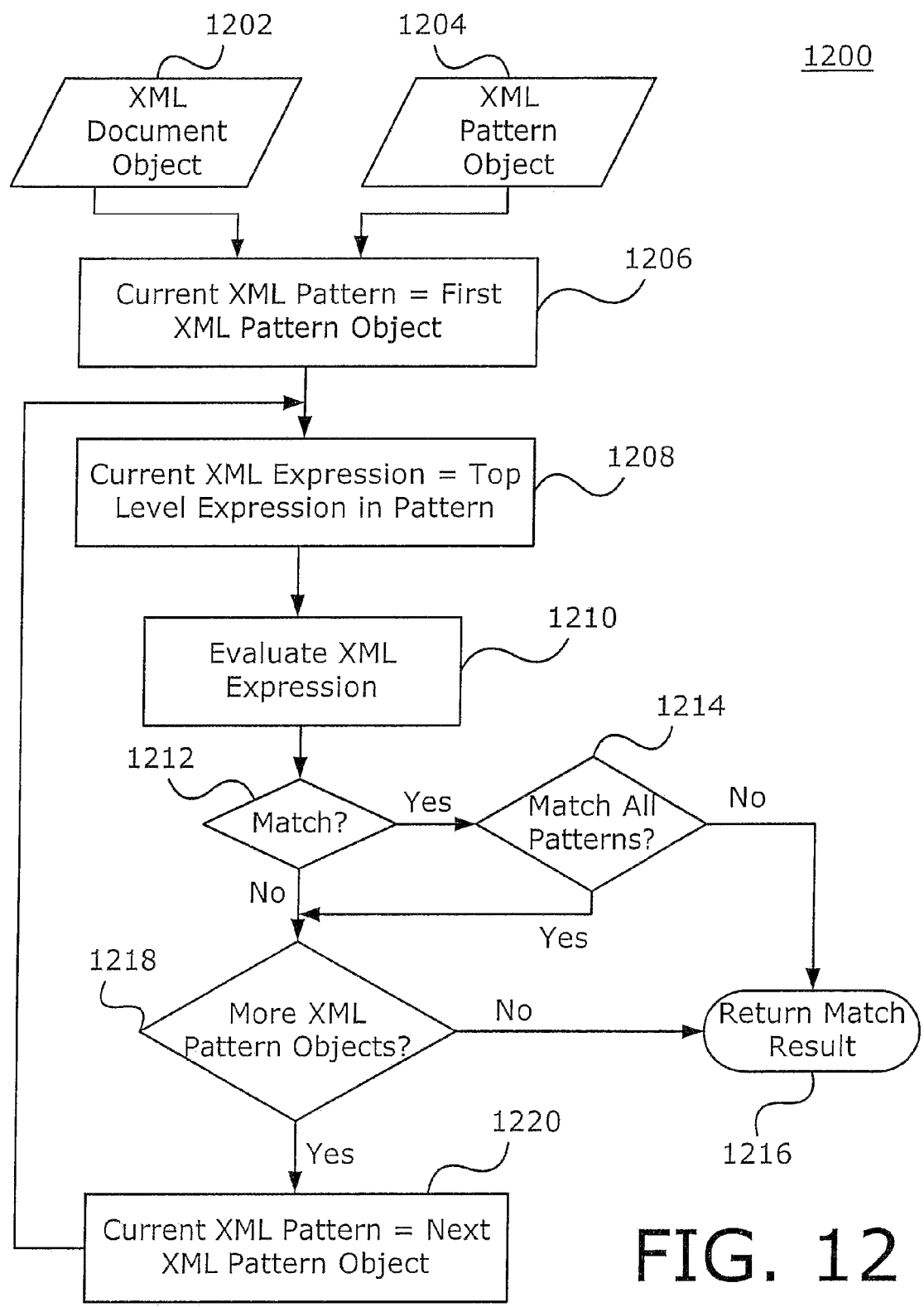
FIG. 12 is a block flow diagram of a pattern matching algorithm in accordance with one embodiment of the invention.

FIG. 12 is a block flow diagram of a pattern matching algorithm in accordance with one embodiment of the invention. FIG. 12 illustrates a programming logic 1200 that may be implemented, for example, as part of content based switching decision logic 710. An XML document object is generated at block 1202. An XML pattern object is generated at block 1204. The XML pattern object is designated as the current XML pattern at block 1206. The current XML expression is designated as the top level expression in the XML pattern object at block 1208. The current XML expression is evaluated at block 1210. A determination is made whether there is a match of the current XML expression by the XML document object at block 1212. If there is a match at block 1212, a determination is made as to whether all the XML pattern objects must be matched at block 1214. If all the XML pattern objects do not need to be matched at block 1214, the match result is returned at block 1216. If all the XML pattern objects must be matched at block 1214, a determination is made whether there are any more XML pattern objects at block 1218. If there are no more XML pattern objects to be matched at block 1218, the match result is returned at block 1216. If there are more XML pattern objects to be matched at block 1218, the next pattern object is retrieved and designated the current XML pattern object at block 1220, and control is passed to block 1208.

Figure 13:
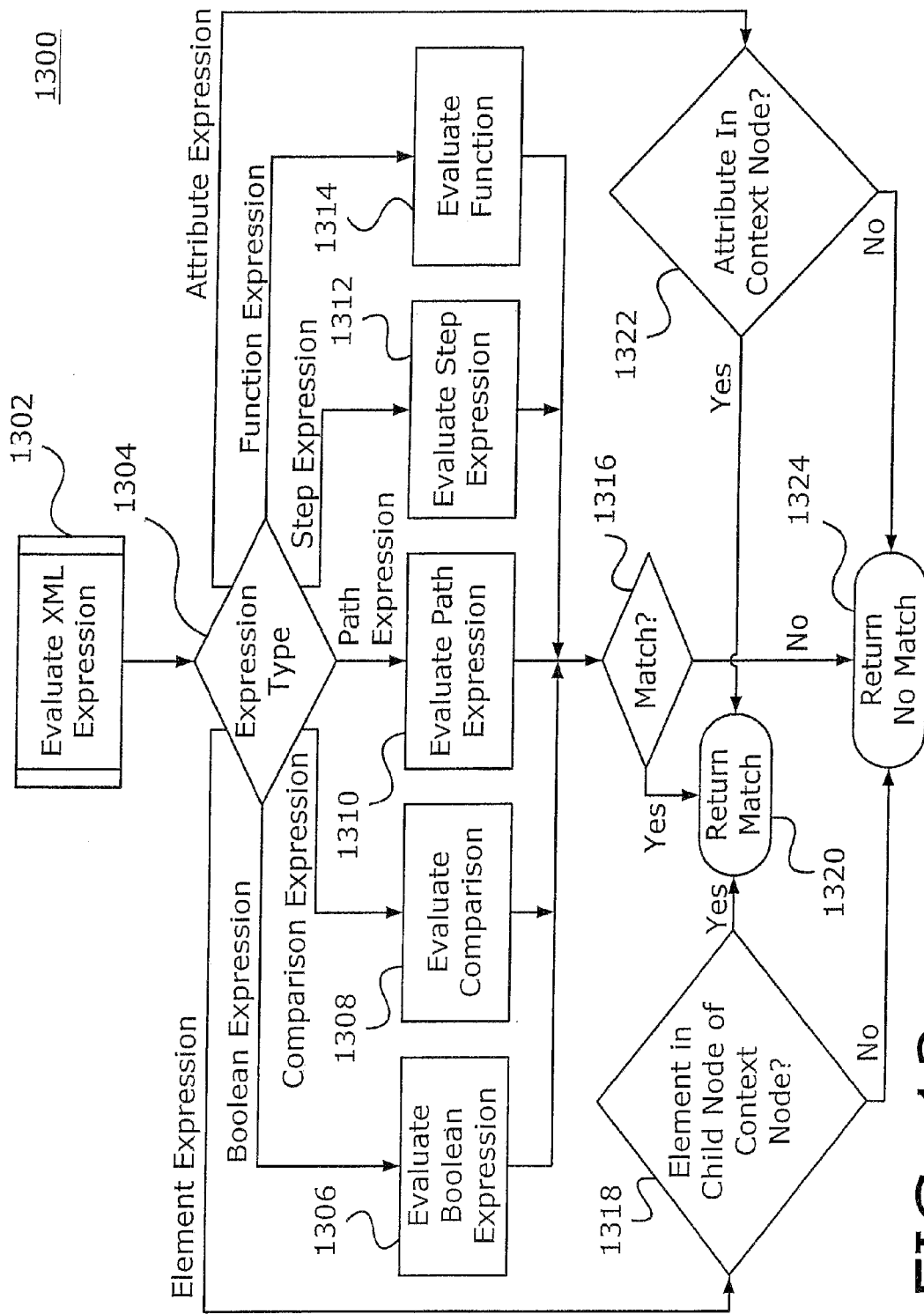
FIG. 13 is a block flow diagram to evaluate an XML expression in accordance with one embodiment of the invention.

FIG. 13 is a block flow diagram to evaluate an XML expression in accordance with one embodiment of the invention. FIG. 13 illustrates a programming logic 1300 that may be implemented as part of block 1210 discussed with reference to FIG. 12. A determination is made as to the expression type at block 1304.

If the expression type is an elemental expression, a determination is made as to whether the element is in the child node of the context node at block 1318. If the element is in the child node of the context node at block 1318, a match is returned at block 1320. If the element is not in the child node of the context node at block 1318, a no match result is returned at block 1324.

If the expression type is a Boolean expression, the Boolean expression is evaluated at block 1306. A determination is made as to whether a match has occurred with the XML document object at block 1316. If a match has occurred at block 1316, a match is returned at block 1320. If a match has not occurred at block 1316, a no match result is returned at block 1324.

If the expression type is a comparison expression, the comparison expression is evaluated at block 1308. A determination is made as to whether a match has occurred with the XML document object at block 1316. If a match has occurred at block 1316, a match is returned at block 1320. If a match has not occurred at block 1316, a no match result is returned at block 1324.

If the expression type is a path expression, the path expression is evaluated at block 1310. A determination is made as to whether a match has occurred with the XML document object at block 1316. If a match has occurred at block 1316, a match is returned at block 1320. If a match has not occurred at block 1316, a no match result is returned at block 1324.

If the expression type is a step expression, the step expression is evaluated at block 1312. A determination is made as to whether a match has occurred with the XML document object at block 1316. If a match has occurred at block 1316, a match is returned at block 1320. If a match has not occurred at block 1316, a no match result is returned at block 1324.

If the expression type is a function expression, the function expression is evaluated at block 1314. A determination is made as to whether a match has occurred with the XML document object at block 1316. If a match has occurred at block 1316, a match is returned at block 1320. If a match has not occurred at block 1316, a no match result is returned at block 1324.

If the expression type is an attribute expression, a determination is made as to whether the attribute is in the context node at block 1322. If the attribute expression is in the context node at block 1322, a match is returned at block 1320. If the attribute expression is not in the context node at block 1322, a no match result is returned at block 1324.

Figure 14:
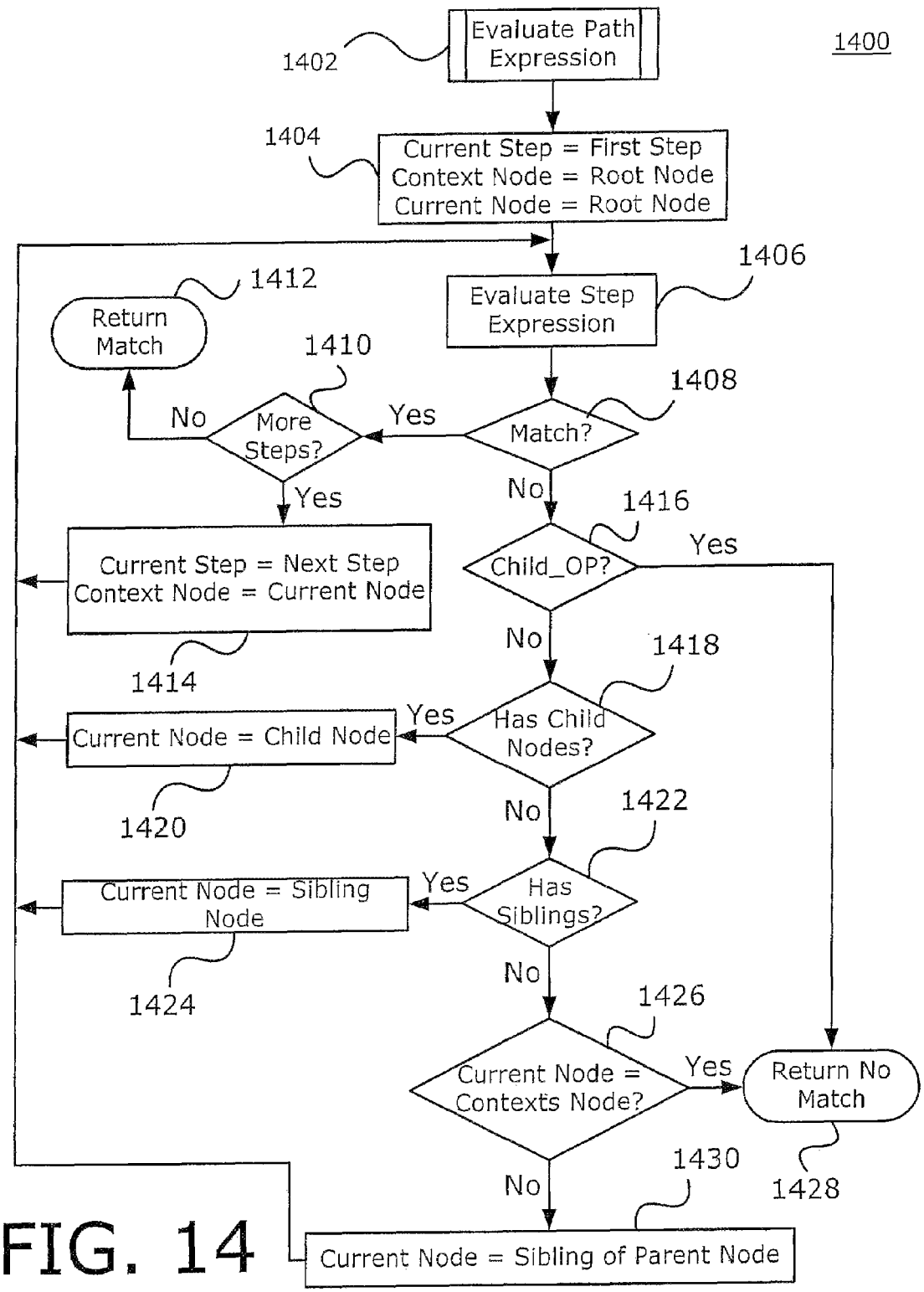
FIG. 14 is a block flow diagram to evaluate a path expression in accordance with one embodiment of the invention.

FIG. 14 is a block flow diagram to evaluate a path expression in accordance with one embodiment of the invention. FIG. 14 illustrates a programming logic 1400 that may be implemented as part of block 1310 as described with reference to FIG. 13. The path expression is evaluated at block 1402. The first step is designated as the current step, the root node is designated as the context node, and the root node is designated as the current node at block 1404. A step expression of the path expression is evaluated at block 1406.

A determination is made as to whether the step expression matches the XML document object at block 1408. If there is a match at block 1408, a determination is made as to whether the path expression has any more step expressions at block 1410. If there are no more step expressions at block 1410, a match result is returned at block 1412. If there are more step expressions at block 1410, the next step is designated as the current step and the current node is designated as the context node at block 1414, and control is passed to block 1406.

If there is no match at block 1408, a determination is made as to whether the step expression is a "child_OP" at block 1416. If the step expression is a "child_OP" at block 1416, a no match result is returned at block 1428. If the step expression is not a "child_OP" at block 1416, a determination is made as to whether the current node has any child nodes at block 1418. If there is a child node at block 1418, the child node is designated as the current node at block 1420 and control is returned to block 1406. If there is no child node at block 1418, then a determination is made as to whether the current node has any siblings at block 1422. If the current node has a sibling at block 1422, the sibling node is designated as the current node at block 1424, and control is returned to block 1406. If the current node does not have a sibling at block 1422, a determination is made as to whether the context node is the same as the current node at block 1426. If the context node is the same as the current node at block 1426, a no match result is returned at block 1428. If the context node is not the same as the current node at block 1426, a sibling of the parent node is designated as the current node at block 1430, and control is passed to block 1406.

Figure 15:
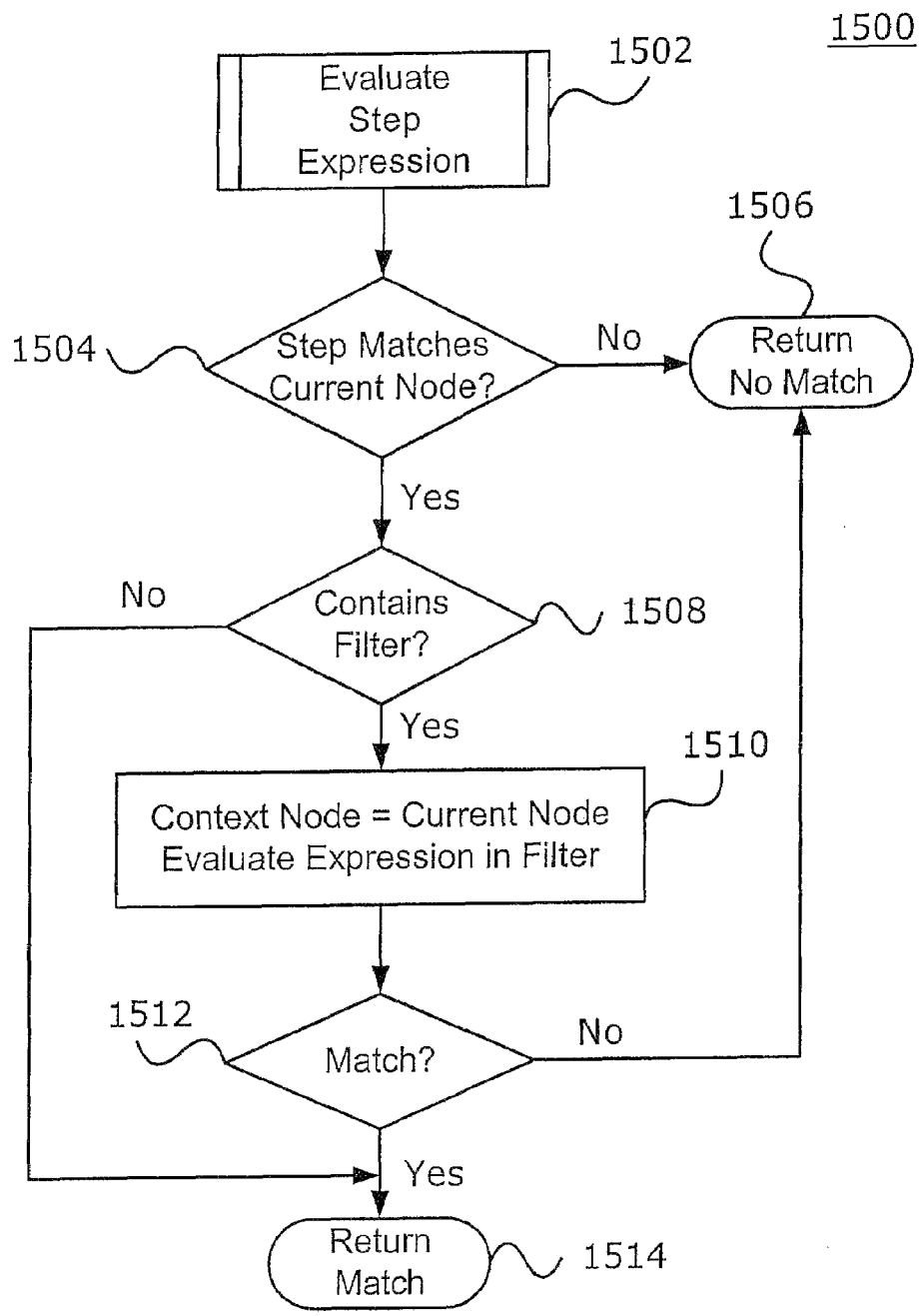
FIG. 15 is a block flow diagram to evaluate a step expression in accordance with one embodiment of the invention.

FIG. 15 is a block flow diagram to evaluate a step expression in accordance with one embodiment of the invention. FIG. 15 illustrates a programming logic 1500 that may be implemented as part of block 1312 described with reference to FIG. 13, and/or block 1406 described with reference to FIG. 14. The step expression is evaluated at block 1502. A determination is made as to whether the step expression matches the current node at block 1504. If the step expression does not match the current node at block 1504, a no match result is returned at block 1506. If the step expression matches the current node at block 1504, a determination is made as to whether the step expression contains a filter at block 1508. If the step expression does not contain a filter at block 1508, a match result is returned at block 1514. If the step expression does contain a filter at block 1508, the current node is designated as the context node and the filter expression is evaluated at block 1510. A determination is made as to whether the filter expression is matched at block 1512. If the filter expression is matched at block 1512, a match result is returned at block 1514, otherwise a no match result is returned at block 1506.

Figure 16:
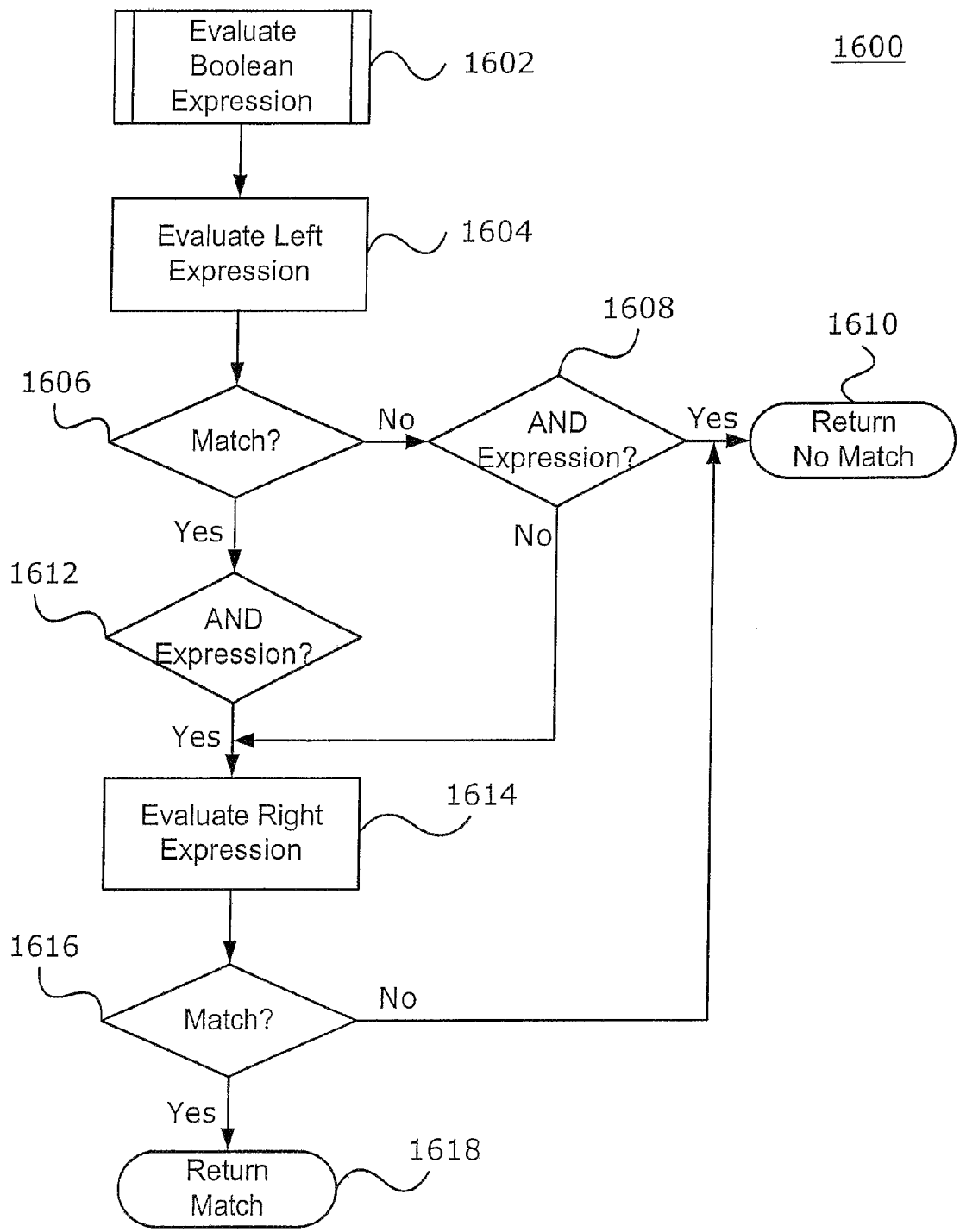
FIG. 16 is a block flow diagram to evaluate a Boolean expression in accordance with one embodiment of the invention.

FIG. 16 is a block flow diagram to evaluate a Boolean expression in accordance with one embodiment of the invention. FIG. 16 illustrates a programming logic 1600 that may be implemented as part of block 1306 as described with reference to FIG. 13. A Boolean expression is evaluated at block 1602. The left expression is evaluated at block 1604. A determination is made as to whether the left expression is matched at block 1606. If the left expression is not matched at block 1606, a determination is made as to whether the Boolean expression is an "AND" expression at block 1608. If the Boolean expression is an "AND" expression at block 1608, a no match result is returned at block 1610. If the Boolean expression is not an "AND" expression at block 1608, the right expression is evaluated at block 1614. If the left expression is matched at block 1606, a determination is made as to whether the Boolean expression is an "AND" expression at block 1612. If the Boolean expression is an "AND" expression at block 1612, the right expression is evaluated at block 1614. A determination is made as to whether the right expression is matched at block 1616. If the right expression is not matched at block 1616, a no match result is returned at block 1610, otherwise a match result is returned at block 1618.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A network apparatus, comprising:
   a document parser to parse a document having transaction information and to create a document object from said transaction information;
   a pattern parser to parse pattern information of a pattern for one or more elements according to a predefined pattern object data structure and to place said elements in appropriate blocks within said pattern object data structure;
   a pattern object generator to receive said pattern information of a pattern and to create a pattern object from said pattern information; and
   content based switching decision logic to make a switching decision for a message based upon a comparison of said document object with said pattern object, said pattern object contains at least one expression, and said content based switching logic evaluates said at least one expression for a match with said document object.

2. The network apparatus of claim 1, further comprising a document object generator to receive said document having transaction information.

3. The network apparatus of claim 1, wherein said transaction information and said pattern information represent XML information.

4. The network apparatus of claim 1, wherein said document object represents a logical tree of said transaction information.

5. The network apparatus of claim 1, further comprising an output interface to receive a message from a network and to receive said switching decision from said content based switching decision logic, said output interface to route or switch the received message to one of a plurality of processing nodes to process said message based upon said switching decision.

6. The network apparatus of claim 1, wherein said pattern object comprises at least one sub-expression represented by an expression object.

7. The network apparatus of claim 1, wherein said expression comprises an expression type and expression data.

8. A system comprising:
   a network apparatus comprising a content based message director coupled to a wireless telephone, said content based message director comprising:
   a document parser to parse said document and create a document object from said transaction information;
   a pattern parser to parse pattern information of a pattern for one or more elements according to a predefined pattern object data structure and to place said elements in appropriate blocks within said pattern object data structure;

a pattern object generator to receive said pattern information of a pattern and to create a pattern object from said pattern information; and content based switching decision logic to make a switching decision for a message based upon a comparison of said document object with said pattern object, said pattern object contains at least one expression, and said content based switching logic evaluates said at least one expression for a match with said document object.

9. The system of claim 8, further comprising a document object generator to receive said document having transaction information.

10. The system of claim 8, further comprising an output interface to receive a message from a network and to receive said switching decision from said content based switching decision logic, said output interface to route or switch the received message to one of a plurality of processing nodes to process said message based upon said switching decision.

11. The system of claim 8, wherein said transaction information and said pattern information represent XML information.

12. A method comprising:
parsing, by a document parser, a document having transaction information;
creating, by said document parser, a document object using said transaction information;
parsing, by a pattern parser, pattern information of a pattern for one or more elements according to a predefined pattern object data structure;
placing said elements in appropriate blocks within said pattern object data structure;
creating a pattern object from said pattern information;
making a switching decision, using content based switching decision logic, for a message based upon a comparison of said document object with said pattern object; and
evaluating, using said content based switching logic, at least one expression contained in said pattern object for a match with said document object.

13. The method of claim 12, further comprising receiving a message from a network,
receiving said switching decision, and routing or switching the received message to one of a plurality of processing nodes to process said message based upon said switching decision.

14. The method of claim 12, wherein said transaction information and said pattern information represent XML information.

15. An article comprising:
a storage medium;
said storage medium including stored instructions that, when executed by a processor, result in parsing a document having transaction information, creating a document object using said transaction information, parsing pattern information of a pattern for one or more elements according to a predefined pattern object data structure, placing said elements in appropriate blocks within said pattern object data structure, creating a pattern object from said pattern information, making a switching decision for a message based upon a comparison of said document object with said pattern object, and evaluating at least one expression contained in said pattern object for a match with said document object.

16. The article of claim 15, wherein the stored instructions, when executed by a processor, further result in receiving a message from a network, receiving said switching decision, and routing or switching the received message to one of a plurality of processing nodes to process said message based upon said switching decision.

17. The article of claim 15, wherein said transaction information and said pattern information represent XML information.

* * * * *